(12) United States Patent
Yuan et al.

(10) Patent No.: US 10,406,480 B2
(45) Date of Patent: Sep. 10, 2019

(54) FILTER FOR REMOVING MERCURY IN HIGH-PURITY GASES OR AEROSOL

(71) Applicant: Honglin Yuan, Xi'an (CN)

(72) Inventors: Honglin Yuan, Xi'an (CN); Zhian Bao, Xi'an (CN); Xu Liu, Xi'an (CN); Peng Liang, Xi'an (CN)

(73) Assignee: Honglin Yuan, Xi'an (CN)

( * ) Notice: Subject to any disclaimer, the term of this patent is extended or adjusted under 35 U.S.C. 154(b) by 105 days.

(21) Appl. No.: 15/836,870

(22) Filed: Dec. 10, 2017

(65) Prior Publication Data

US 2018/0117528 A1   May 3, 2018

Related U.S. Application Data

(63) Continuation of application No. PCT/CN2016/080211, filed on Apr. 26, 2016.

(30) Foreign Application Priority Data

Aug. 11, 2015 (CN) .......................... 2015 1 0488241

(51) Int. Cl.
| | | |
|---|---|---|
| *B01D 53/64* | (2006.01) | |
| *G01N 1/34* | (2006.01) | |
| *B01D 53/04* | (2006.01) | |
| *B01D 53/82* | (2006.01) | |

(52) U.S. Cl.
CPC ......... *B01D 53/64* (2013.01); *B01D 53/0407* (2013.01); *G01N 1/34* (2013.01); *B01D 53/82* (2013.01); *B01D 2253/1122* (2013.01); *B01D 2255/106* (2013.01); *B01D 2257/602* (2013.01)

(58) Field of Classification Search
CPC .... B01D 53/0407; B01D 53/64; B01D 53/82; B01D 2253/1122; B01D 2255/106; B01D 2257/602; G01N 1/34
USPC ............ 96/108, 131, 416; 55/440, 462, 464
See application file for complete search history.

(56) References Cited

U.S. PATENT DOCUMENTS

| | | | | |
|---|---|---|---|---|
| 3,232,033 A | * | 2/1966 | Williston ........... | B01D 39/2017 55/524 |
| 4,419,107 A | * | 12/1983 | Roydhouse ............ | B01D 53/64 420/498 |
| 2014/0373715 A1 | * | 12/2014 | Alper ................... | B01D 46/002 95/285 |

* cited by examiner

*Primary Examiner* — Frank M Lawrence, Jr.
(74) *Attorney, Agent, or Firm* — Wayne & Ken, LLC; Tony Hom (57) ABSTRACT

The invention discloses a filter for removing mercury in high-purity gases or aerosol, including a cylindrical outer chamber, both ends of the cylindrical outer chamber are provided with an inlet air pipe and an outlet air pipe, multiple sets of stepped liners and gradually deformed jackets mounted mutually are provided together inside the outer chamber. A stepped liner is provided between two adjacent gradually deformed jackets; a 2-10 μm gold-plated layer is provided on step surfaces of the stepped liners and step holes of the gradually deformed jackets, a gap channel is formed between step surfaces of stepped liners and step holes of gradually deformed jackets, the gap channel is communicated with the inlet air pipe and the outlet air pipe. The gold-plated layer absorbs mercury to form gold amalgam and remove the mercury, making it possible to analyze ultra-low-level Pb isotopes in minerals, which is unachievable in micro-area analysis.

9 Claims, 6 Drawing Sheets

FILTER FOR REMOVING MERCURY IN HIGH-PURITY GASES OR AEROSOL

FIELD OF THE INVENTION

The present invention relates to a filter for removing high-purity gases or mercury in aerosol, which can be used in current micro-area analysis technical. For example, the application research of Pb isotopes analysis is carried out by laser ablation system quadrupole inductively coupled plasma mass spectrometry, multiple collector plasma mass spectrometry and high resolution plasma mass spectra (including LA-Q-ICPMS, LA-HR-ICPMS and LA-MC-ICPMS). The application research includes direct and accurate analysis of trace amount of Pb isotopes in uranium-Pb dating of zircone, archaeological samples and single minerals (such as sulfide, silicate minerals, etc.).

BACKGROUND OF THE INVENTION micro-area analysis technique has been developed rapidly with the research progress of new theory and new laser, and is in-situ micro sampling technique realizing the micro-area analysis. Laser ablation technology is widely used because of fast analysis, high accuracy of analysis results, relatively low acquisition and analysis cost. The laser ablation technology is used in combination with quadrupole or high resolution plasma mass spectrometry to analyze the content of the main and trace elements of the sample and the composition of some isotopes, and is used in combination with the multiple collector plasma mass spectrometry to precisely analyze various isotopes of different types of samples. Therefore, micro-area analysis technique is widely used in the field of earth sciences, archaeological science, material science, bioscience, criminal investigation principle, etc.

The fundamental principle of laser ablation technology is that laser focuses on the position to be analyzed of the surface of the sample in the sample chamber to ablate by laser ablation system, the generated ablation particles are transferred to the plasma mass spectra by transmission pipe using carrier gas (usually helium) to be ionized and be analyzed, so that the content or isotopic composition of the sample is obtained.

Analysis of Pb isotope in the micro-area of samples zone provides specific information of samples, for example, in geosciences, it can be used to study the geological process experienced by the rock mass where the geological sample is located; in environmental science, it can be used to study the sources of environmental pollutants; in archeology science, it can be used to study samples of mineral source areas, etc., therefore, analysis of Pb isotopes of different samples in these studies by laser ablation plasma mass spectrometry is of great significance. However, because the carrier gas and support gas for plasma (Ar) contain trace amount of Hg, the presence of these Hg has seriously affected the accurate determination of 204Pb by micro-area analysis of Pb isotopes, and 204Pb belongs to the low abundance (ordinary Pb has four isotopes, 204Pb, 206Pb, 207Pb and 208Pb, respectively, with corresponding abundances of 1.4245%, 24.1447%, 22.0827%, 52.3481%, the Pb isotope ratio commonly used in this study refers to 206Pb/204Pb, 207Pb/204Pb and 208Pb/204Pb), since the low abundance 204Pb that is interfered is in the denominator, trace amounts of Hg (204Hg interferes 204Pb analysis) can have a serious effect on the accuracy of Pb isotopes analysis. And some samples, such as chalcopyrite, pyrite, sphalerite, etc. in deposit studies, often contain higher levels of Hg, or some samples contain lower levels of Pb (less than 5 ppm), so that these samples can not be accurately analyzed in current Laser Ablation-inductively Coupled Plasma Mass Spectrometry (LA-ICPMS).

SUMMARY OF THE INVENTION

The object of the present invention is to eliminate the effect of carrier gas and trace amounts of mercury on the accurate measurement of micro-area analyzing Pb isotope 204Pb.

For this purpose, the present invention provides a filter for removing mercury in high-purity gases or aerosol comprises a cylindrical outer chamber, one end of the cylindrical outer chamber (2) is provided with an inlet air pipe and the other end of the cylindrical outer chamber (2) is provided with an outlet air pipe; multiple sets of stepped liners and gradually deformed jackets mounted mutually are provided together inside the outer chamber, the stepped liners are rhombohedron shaped with a circular cross section, and the surface of the rhombohedron is a step surface, steps are distributed orderly from vertexes of both ends to a position with maximum diameter in the middle; the gradually deformed jacket (4) is columnar-shaped, step holes matched with the step surfaces of the stepped liner are distributed from both ends to the center in the axis of the gradually deformed jacket.

An outer diameter of the gradually deformed jacket is the same with an inner diameter of the cylindrical outer chamber, a stepped liner is provided between two adjacent gradually deformed jackets.

A 2-10 µm gold-plated layer is provided on the step surfaces of the stepped liners and the step holes of the gradually deformed jackets, a gap channel is formed between the step surfaces of the stepped liners and the step holes of the gradually deformed jackets, the gap channel is communicated with the inlet air pipe and the outlet air pipe.

A support ring is provided outside the maximum diameter of the middle of the stepped liner, a through-hole is provided on the support ring, an outer circle of the support ring is connected with the inner wall of the gradually deformed jacket to support the stepped liner to form the gap channel between the stepped liner and the gradually deformed jacket.

Step corners on the step surfaces of the stepped liner (1) are provided with an arc chamfering, and the step corners of the step holes of gradually deformed jacket (4) are also provided with the arc chamfering.

The gradually deformed jacket comprises a convex gradually deformed jacket and a flat gradually deformed jacket; step holes are distributed from both ends to the middle of an axial center of the convex gradually deformed jacket in axial, an expanding area is provided in the middle of the convex gradually deformed jacket.

Mounting holes are provided on both ends of the flat gradually deformed jacket, step holes are distributed from bottom of the mounting hole to the axial center of the flat gradually deformed jacket, so that the flat gradually deformed jacket is transparent.

An external diameter of the convex gradually deformed jacket is equal to a pore size of the mounting hole, and the external diameter of the expanding area is equal to the external diameter of the flat gradually deformed jacket, both ends of the convex gradually deformed jacket are provided in different mounting holes of the flat gradually deformed jacket, and located by the expanding areas.

An O-shaped seal ring is provided on a mounting surface between the convex gradually deformed jacket and the flat gradually deformed jacket.

The beneficial effects of the present invention:

1. The contact surface of gas or aerosol and gold is expanded, the gas path is without obstruction, the structure is simple and the operation is easy to be implemented by gradually deformed design.

2. The pulsed laser ablation aerosols have a better mixing effect due to multiple mixing and dispersion of aerosols, greatly improving the stability of the analytical signals, so that the results of Pb isotope analysis are more accurate.

3. The outer surface of the inner liner and the inner surface of the jacket are equal in distance, and corresponding corners are provided with arc chamferings so as to avoid rotational flow, vortex and dead angle, and also avoid the possibility of aerosol mutual contamination between different samples when the aerosol passes through, improving the analysis accuracy.

4. Both the outer surface of the inner liner and the inner surface of the outer jacket have a gold plating layer of 2-10 μm, which greatly reduces the development cost of the equipment without changing the removing effect of mercury.

BRIEF DESCRIPTION OF THE DRAWINGS

The content of the present invention is described in detail below with reference to the accompanying drawings.

In figures, 1—stepped liner; 2—outer chamber; 3—inlet air pipe; 4—gradually deformed jacket; 5—outlet air pipe; 6—gap channel; 7—convex gradually deformed jacket; 8—flat gradually deformed jacket; 9—support ring; 10—expanding area; 11—mounting hole.

DETAILED DESCRIPTION OF THE INVENTION

Embodiment 1

The embodiment provides a filter for removing high-purity gases or mercury in aerosol, as shown in FIG. 1 to FIG. 5, the filter comprises a cylindrical cylindrical outer chamber 2, one end of the cylindrical outer chamber 2 is provided with an inlet air pipe 3 and the other end of the cylindrical outer chamber 2 is provided with an outlet air pipe 5; multiple sets of stepped liners 1 and gradually deformed jackets 4 mounted mutually are provided together inside the cylindrical outer chamber 2, the stepped liners 1 are rhombohedron shaped, cross sections of stepped liners 1 are circular shaped, and the surface of the rhombohedron is step surface, steps are distributed orderly from vertexes of both ends to the position with maximum diameter in the middle; the gradually deformed jacket 4 is columnar-shape, step holes matched with step surface of the stepped liner 1 are distributed from both ends to the center in the axis of the gradually deformed jacket 4.

Figure 1:
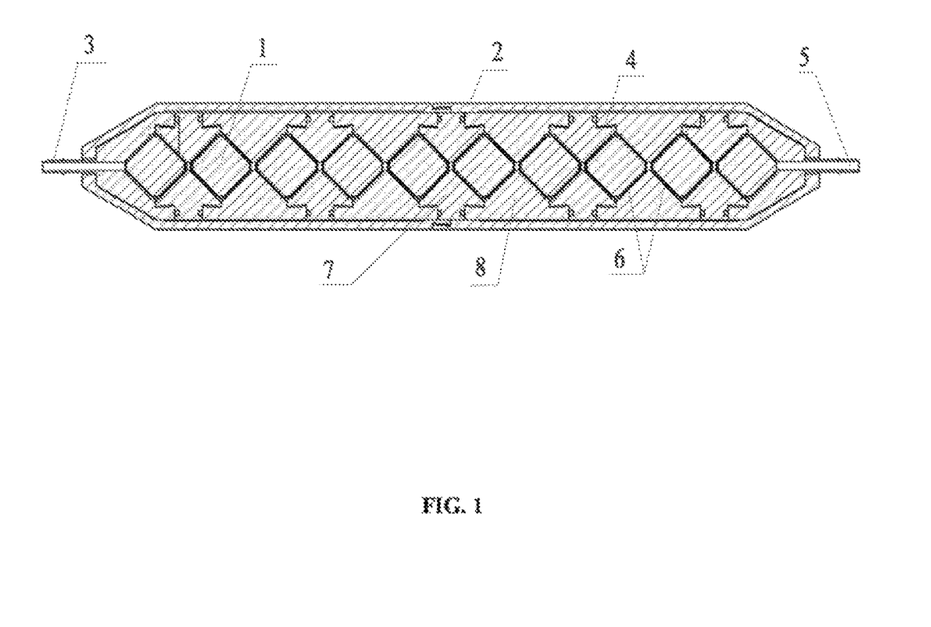
FIG. 1 is a cross-sectional view of a filter for removing high-purity gases or mercury in aerosol of the present invention.

The external diameter of the gradually deformed jacket 4 is equal to the internal diameter of the cylindrical outer chamber, a stepped liner 1 is provided between two adjacent gradually deformed jackets 4.

A 2-10 μm gold-plated layer is provided on the step surfaces of the stepped liners 1 and step holes of the gradually deformed jackets 4, a gap channel 6 is formed between step surfaces of the stepped liners 1 and step holes of the gradually deformed jackets 4, the gap channel 6 is communicated with the inlet air pipe 3 and the outlet air pipe 5.

High purity gas or aerosol is introduced into the device by the inlet air pipe 3, high purity gas or aerosol gets through the filter without restriction and finally is led out by outlet air pipe 5. After the high purity gas or aerosol is introduced into the device, the high purity gas or aerosol contacts repeatedly and sufficiently with the gold plated layer on the surface of the stepped liner 1 and in the step holes of the gradually deformed jacket 4 due to the function of the step surface of the stepped liner 1 and the step holes of the gradually deformed jacket 4, so that the high purity gas or aerosol reacts with the Au to form gold amalgam to remove the Hg. Meanwhile, when the aerosol passes through the filter, the aerosol is dispersed and aggregated by gap channel 6, when the aerosol is filtered, the dispersion of aerosol is more uniform, reaching homogenization effect.

Embodiment 2

Figure 2:
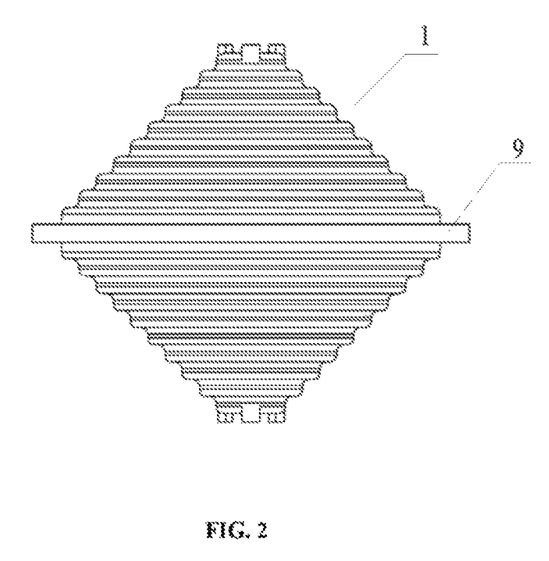
FIG. 2 is a structural view of the stepped liner of the present invention.
Figure 3:
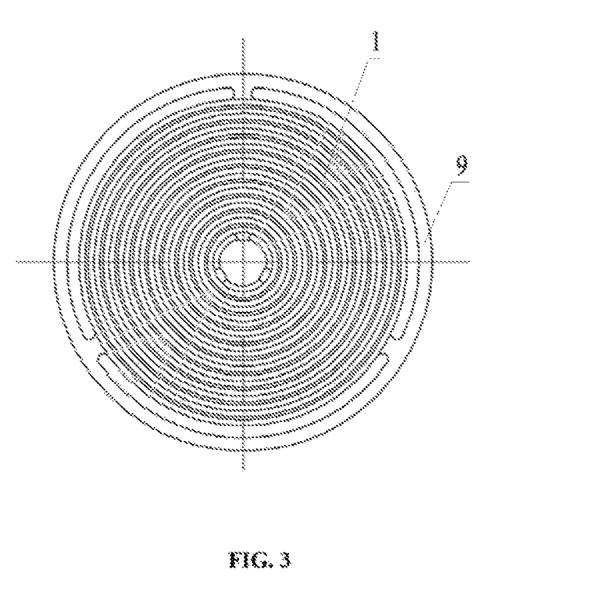
FIG. 3 is a left view of the stepped liner of the present invention.

This embodiment is further improved based on embodiment 1, as shown in FIG. 2 and FIG. 3, a support ring 9 is provided outside the maximum diameter of the middle of the stepped liner 1, a through-hole is provided on the support ring 9, an outer circle of the support ring 9 is connected with the inner wall of the gradually deformed jacket 4 to support the stepped liner 1 to form the gap channel 6 between the stepped liner 1 and the gradually deformed jacket 4.

The gap channels 6 between the stepped liner 1 and the gradually deformed jacket 4 are the same under effect of the support ring 9 and without dead angle, so that aerosol passes successfully in the channel.

Further, the step corners on the step surface of the stepped liner 1 are provided with arc chamferings, and the step corners of step holes of gradually deformed jacket 4 are also provided with arc chamferings, so that the gas or aerosol passes through more successfully without dead volume.

High purity gas or aerosol is continuously dispersed on the steps in the gap channel 6, aggregated on the terminal point of the step, and dispersed once again on the next step in the gap channel 6, and high purity gas or aerosol is continually dispersed and aggregated together. Aerosol has better homogenization effect on the pulse signal because the aerosol changes direction repeatedly in the channel, dispersed and aggregated repeatedly in the process of removing Hg from the aerosol, so that analysis signal is more stable, which removes mercury signal from carrier gas, and removes mercury from aerosol, greatly improving the reliability of low-level Pb isotopes by Laser Ablation-inductively Coupled Plasma Mass Spectrometry (LA-ICPMS)

Embodiment 3

Figure 4:
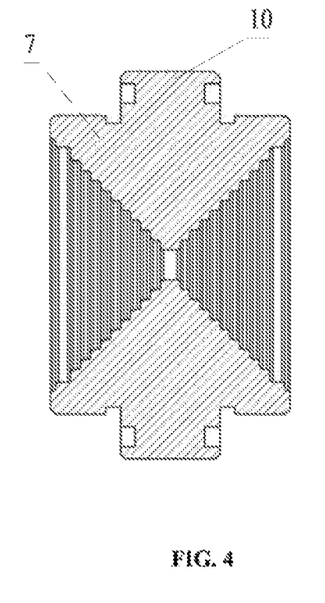
FIG. 4 is a structural view of the convex gradually deformed jacket of the present invention.

The gradually deformed jacket 4 is further illustrated in this embodiment based on embodiment 1 and embodiment 2. In the present embodiment, the gradually deformed jacket (4) comprises a convex gradually deformed jacket (7) and a flat gradually deformed jacket (8), as shown in FIG. 4, step holes are distributed from both ends to the middle of the axial center of the convex gradually deformed jacket (7) in axial, an expanding area (10) is provided in the middle of the convex gradually deformed jacket (7) to make the convex gradually deformed jacket (7) transparent. As show in FIG. 5, mounting holes (11) are provided on both ends of the flat gradually deformed jacket (8), step holes are distributed from bottom of the mounting hole (11) to the axial center of the flat gradually deformed jacket (8), so that the flat gradually deformed jacket (8) is transparent.

Figure 5:
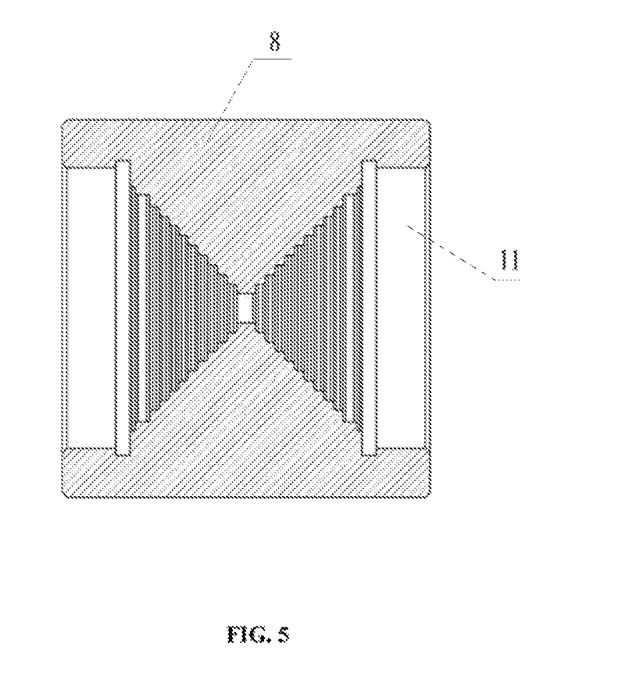
FIG. 5 is a structural view of the flat gradually deformed jacket in the present invention.

The external diameter of the convex gradually deformed jacket (7) is equal to the pore size of the mounting hole (11), the external diameter of the expanding area (10) is equal to the external diameter of the flat gradually deformed jacket (8), both ends of the convex gradually deformed jacket (7) are provided in different mounting holes (11) of the flat gradually deformed jacket (8), and located by the expanding areas (10).

Figure 6:
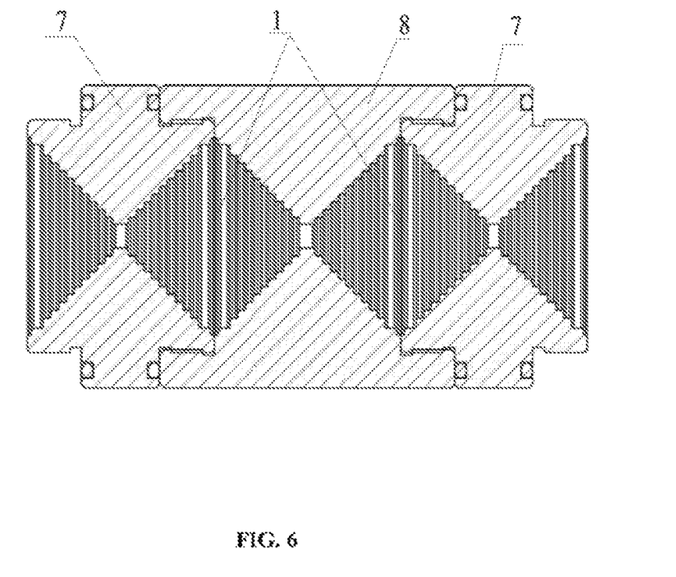
FIG. 6 is a mutual installation view of the stepped liner, the convex gradually deformed jacket and the flat gradually deformed jacket.

Combining FIG. 1 and FIG. 6, the outer diameters of the convex gradually deformed jacket (7) and the flat gradually deformed jacket (8) are both at the inner wall of the cylindrical outer chamber 2, of course, both ends of the cylindrical outer chamber 2 in this embodiment have a cambered surface, correspondingly, the flat gradually deformed jacket (8) here also has a corresponding shape adjustment so as to meet the installation requirements. High purity gas or aerosol enters into the inlet air pipe 3, the inlet air pipe 3 is communicated with the gas channel 6, and the high purity gas or aerosol is dispersed and guided down along the step, trace amounts of Hg in the high purity gas or aerosol reacts with the Au layer on the step to form Au amalgams, so that Hg is removed. The high purity gas or aerosol is aggregated together in the center of the first convex gradually deformed jacket (7), dispersed along the steps, and aggregated together once again at the center of the first flat gradually deformed jacket (8), dispersed once again along the steps to remove Hg in the high purity gas or aerosol and to form the Au amalgams on the steps, and educed by the outlet pipe 5. In this way, trace mercury in high purity gas or aerosol has been filtered.

In the present embodiment, an O-shaped seal ring is provided on the mounting surface between the convex gradually deformed jacket (7) and the flat gradually deformed jacket (8) to achieve sealing effect, so that the high purity gas or aerosol moves ahead along the path of the inlet air pipe 3, the gap channel 6 and the outlet air pipe 5, and no effusion to other positions.

In conclusion, the filter for removing high-purity gases or mercury in aerosol in the present invention makes it possible to analyze ultra-low-level Pb isotopes in minerals, which is unachievable in micro-area analysis. This is of great significance to the current study of laser ablation Q-ICPMS and MC-ICPMS in zircon dating and single-mineral Pb isotopic composition analysis.

The above embodiments are merely examples of the present invention, and do not limit the protection scope of the present invention. Any designs identical to or similar to the present invention shall fall within the protection scope of the present invention.

What is claimed is:

1. A filter for removing mercury in high-purity gases or aerosol, comprising a cylindrical outer chamber (2); two ends of the cylindrical outer chamber (2) are respectively provided with an inlet air pipe (3) and an outlet air pipe (5); wherein, multiple sets of stepped liners (1) and gradually deformed jackets (4) mounted mutually are provided together inside the cylindrical outer chamber (2); the stepped liners (1) are rhombohedron shaped with a circular cross section, and the surface of the rhombohedron is a step surface; steps are distributed orderly from vertexes of both ends to a position with maximum diameter in the middle; the gradually deformed jacket (4) is columnar-shaped, step holes matched with the step surfaces of the stepped liner (1) are distributed from both ends to the center in the axis of the gradually deformed jacket (4); an outer diameter of the gradually deformed jacket (4) is the same with an inner diameter of the gradually deformed jacket (4); a stepped liner (1) is provided between two adjacent gradually deformed jackets (4); a 2-10 μm gold-plated layer is provided on the step surfaces of the stepped liners (1) and the step holes of the gradually deformed jackets (4); a gap channel (6) is formed between the step surfaces of the stepped liners (1) and the step holes of the gradually deformed jackets (4), and the gap channel (6) is communicated with the inlet air pipe (3) and the outlet air pipe (5).

2. The filter for removing mercury in high-purity gases or aerosol of claim 1, wherein, a support ring (9) is provided outside the maximum diameter of the middle of the stepped liner (1); a through-hole is provided on the support ring (9); an outer circle of the support ring (9) is connected with the inner wall of the gradually deformed jacket (4) to support the stepped liner (1), forming the gap channel (6) between the stepped liner (1) and the gradually deformed jacket (4).

3. The filter for removing mercury in high-purity gases or aerosol of claim 1, wherein, step corners on the step surfaces of the stepped liner (1) are provided with an arc chamfering, and the step corners of the step holes of gradually deformed jacket (4) are also provided with the arc chamfering.

4. The filter for removing mercury in high-purity gases or aerosol of claim 1, wherein, the gradually deformed jacket (4) comprises a convex gradually deformed jacket (7) and a flat gradually deformed jacket (8); step holes are distributed from both ends to the middle of an axial center of the convex gradually deformed jacket (7) in axial, an expanding area (10) is provided in the middle of the convex gradually deformed jacket (7); mounting holes (11) are provided on both ends of the flat gradually deformed jacket (8), step holes are distributed from bottom of the mounting hole (11) to the axial center of the flat gradually deformed jacket (8), so that the flat gradually deformed jacket (8) is transparent; an external diameter of the convex gradually deformed jacket (7) is equal to a pore size of the mounting hole (11), and the external diameter of the expanding area (10) is equal to the external diameter of the flat gradually deformed jacket (8); both ends of the convex gradually deformed jacket (7) are provided in different mounting holes (11) of the flat gradually deformed jacket (8), and located by the expanding area (10).

5. The filter for removing mercury in high-purity gases or aerosol of claim 4, wherein, an O-shaped seal ring is provided on a mounting surface between the convex gradually deformed jacket (7) and the flat gradually deformed jacket (8).

6. The filter for removing mercury in high-purity gases or aerosol of claim 2, wherein, the gradually deformed jacket (4) is divided into a convex gradually deformed jacket (7) and a flat gradually deformed jacket (8); step holes are distributed from both ends to the middle of an axial center of the convex gradually deformed jacket (7) in axial, an expanding area (10) is provided in the middle of the convex gradually deformed jacket (7); mounting holes (11) are provided on both ends of the flat gradually deformed jacket (8), step holes are distributed from bottom of the mounting hole (11) to the axial center of the flat gradually deformed jacket (8), so that the flat gradually deformed jacket (8) is transparent; the external diameter of the convex gradually deformed jacket (7) is equal to the pore size of the mounting hole (11), the external diameter of the expanding area (10) is equal to the external diameter of the flat gradually deformed jacket (8), both ends of the convex gradually deformed jacket (7) are provided in different mounting holes (11) of the flat gradually deformed jacket (8), and located by the expanding area (10).

7. The filter for removing mercury in high-purity gases or aerosol of claim 6, wherein, an O-shaped seal ring is provided on a mounting surface between the convex gradually deformed jacket (7) and the flat gradually deformed jacket (8).

8. The filter for removing mercury in high-purity gases or aerosol of claim 3, wherein, the gradually deformed jacket (4) is divided into the convex gradually deformed jacket (7) and flat gradually deformed jacket (8); step holes are distributed from both ends to the middle of an axial center of the convex gradually deformed jacket (7) in axial, an expanding area (10) is provided in the middle of the convex gradually deformed jacket (7); mounting holes (11) are provided on both ends of the flat gradually deformed jacket (8), step holes are distributed from bottom of the mounting hole (11) to the axial center of the flat gradually deformed jacket (8), so that the flat gradually deformed jacket (8) is transparent; the external diameter of the convex gradually deformed jacket (7) is equal to the pore size of the mounting hole (11), the external diameter of the expanding area (10) is equal to the external diameter of the flat gradually deformed jacket (8), both ends of the convex gradually deformed jacket (7) are provided in different mounting holes (11) of the flat gradually deformed jacket (8), and located by the expanding area (10).

9. The filter for removing mercury in high-purity gases or aerosol of claim 8, wherein, an O-shaped seal ring is provided on a mounting surface between the convex gradually deformed jacket (7) and the flat gradually deformed jacket (8).

* * * * *